(12) United States Patent
Tedgui et al.

(10) Patent No.: US 8,187,818 B2
(45) Date of Patent: May 29, 2012

(54) USE OF SPLA$_2$ ACTIVITY FOR THE DIAGNOSIS OF A CARDIOVASCULAR EVENT

(75) Inventors: Alain Tedgui, Paris (FR); Ziad Mallat, Herbeville (FR); Joëlle Benessiano, Paris (FR)

(73) Assignees: Assistance Publique—Hopitaux de Paris, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 364 days.

(21) Appl. No.: 12/375,954

(22) PCT Filed: Jul. 31, 2007

(86) PCT No.: PCT/IB2007/002211
§ 371 (c)(1),
(2), (4) Date: Apr. 27, 2009

(87) PCT Pub. No.: WO2008/015546
PCT Pub. Date: Feb. 7, 2008

(65) Prior Publication Data
US 2009/0325194 A1    Dec. 31, 2009

(30) Foreign Application Priority Data
Jul. 31, 2006    (EP) ................................ 06291238

(51) Int. Cl.
*G01N 33/53*    (2006.01)

(52) U.S. Cl. .......................................... 435/7.1; 436/518
(58) Field of Classification Search .................. None
See application file for complete search history.

(56) References Cited

U.S. PATENT DOCUMENTS

| | | | |
|---|---|---|---|
| 7,829,086 B2 * | 11/2010 | Hilbert et al. | 424/133.1 |
| 2006/0263357 A1 * | 11/2006 | Tedder et al. | 424/144.1 |
| 2008/0138336 A1 * | 6/2008 | Damschroder et al. | 424/133.1 |

OTHER PUBLICATIONS

Niessen et al. (Cardiovascular Res 2003 vol. 60, p. 68-77).*
Bakoush et al. Kidney International 2001 vol. 60, p. 1904-1909.*
Mayr et al. J. Am. Coll. Cardiol. (2006) 47:2436-43.*

* cited by examiner

*Primary Examiner* — Jacob Cheu
(74) *Attorney, Agent, or Firm* — Young & Thompson (57) ABSTRACT

A method for determining an increased risk of mortality or of a cardiac and/or vascular event in a patient, includes:—determining the sPLA2 activity of the patient as a first risk marker—determining at least the value of a second risk marker chosen among CRP level, IgM IC of apo B 100 level or IgM MDA-LDL level—determining the ratio (odds ratio) between the value of the sPLA2 activity and the value of the second risk marker and comparing it to a predetermined odds ratio, the odds ratio compared to the predetermined odds ratio being indicative of an increased risk of mortality or of a cardiac and/or vascular event. A new micro method adaptation for automated fluorimetric measurement of serum secretory phospholipase A2 is also disclosed.

9 Claims, 2 Drawing Sheets

USE OF SPLA$_2$ ACTIVITY FOR THE DIAGNOSIS OF A CARDIOVASCULAR EVENT

The present invention relates to the use of sPLA$_2$ activity for the diagnosis of a cardiovascular event.

Cardiovascular disorders are among the leading causes of morbidity and mortality in developed countries, making the prevention of those afflictions a major concern of public health.

Inflammation plays a key role in the physiopathology of vulnerable plaque and consequently of coronary events. Measurement of circulating markers of inflammation has attracted considerable interest in the last decade. Among them C-reactive protein (CRP) has been found to be the strongest "novel" biomarker thus far identified for predicting atherothrombic events in apparently healthy individuals and for adding predictive value at all levels of risks based on Framingham score (Ridker P. M. et al., *N. Engl. J. Med.* (2002); 347: 15557-1565). As a result, recent guidelines have recommended that CRP measurement should be considered for patients at intermediate risk of coronary artery disease (CAD) (Pearson T. A. et al. *Circulation* (2003); 107:499-511) However, although measurement of CRP combined with traditional risk factor is a major component in improving risk prediction, there is still substantial room for improvement. A current interest has emerged for evaluating the impact of potential associations of inflammatory for evaluating the impact of potential associations of inflammatory markers in order to improve the prediction of absolute CAD risk in the general population (Ridker P. M. et al., *Circulation* (2004); 109: IV6-19)

Phospholipase A2 (PLA2) enzymes hydrolyze phospholipids at the sn-2 position to generate lysophospholipids and fatty acids (Dennis *J Biol Chem.* (1994) 269:13057-13060) leading to the activation of various immuno-inflammatory processes related to the pathogenesis and complications of atherosclerosis (Hurt-Camejo E. et al., *Circ. Res.* (2001); 89:298-304). One of the most extensively studied PLA2 is a low molecular weight (14 kDa) group IIa secretory PLA2 (sPLA2), shown to be expressed in normal arteries and atherosclerotic plaques (Elinder et al. *Arterioscler Thromb Vasc Biol.* (1997) 17:2257-63) and associated with enhanced susceptibility to atherogenesis in animals (Ivandic B. et al., Castellani L. W. *Arterioscler Thromb Vasc Biol.* (1999) 19:2257-63). Increased plasma concentration of sPLA2 plasma concentration of sPLA2 type IIA has been associated with the risk of coronary events in stable patient (Kugiyama K. et al., *Circulation*, (1999), 100:1280-1284). The role of other types of sPLA2 in atherosclerosis is poorly understood. Recently, it has been shown that direct and accurate measurement of circulating sPLA2 enzyme activity, which encompass several types of sPLA2, is a better indicator of the potential pro-atherogenic properties of these enzymes than the measurement of a particular sPLA2 mass level (Mallat et al., EP No 04 291 825.0). This patent also showed that plasma sPLA2 activity was an independent predictor of death and new or recurrent myocardial infarction in patients with acute coronary syndrome, and provided a better prognostic value than the measurement of sPLA$_2$ type IIA concentration or CRP levels. However, sPLA2 activity and CRP levels are poorly correlated (r=0.47, P<0.0001; EP No 04 291 825.0)

Atherosclerosis is a chronic immuno-inflammatory disease wherein both oxidized lipids and infectious agents are incriminated as possible contributors. In a recent study (Mayr M. et al., *J. Am. Coll. Cardiol.* (2006) 47:2436-43), immunoglobulin (Ig)G and IgM autoantibody titers to copper-oxidized-LDL and malondialdehyde-LDL (OxLDL-AB), IgG and IgM apolipoprotein B-100-immune complexes (ApoB-IC) were measured and evaluated for their relationship to cardiovascular risk factors, chronic infections, and incident/progressive carotid atherosclerosis. This study provides evidence for an association between human oxLDL markers and chronic infections. However, OxLDL autoantibodies and ApoB-IC did not emerge as independent risk predictors of carotid atherosclerosis in multivariate analyses.

One of the aim of the present invention is to provide new combined markers liable to be used for the prognosis and the diagnosis of cardiovascular disorders more reliable than the ones of the prior art, and providing better information than one biomarker alone.

Another aim of the invention is to provide a new prognostic and/or diagnostic method of cardiovascular diseases liable to be meaningful for apparently healthy people or patients with coronary disorders.

Another aim of the invention is to provide a kit intended for diagnosing a cardiac and/or vascular event.

Still another aim of the invention is to enable the screening of efficient therapeutic means in order to prevent and/or treat cardiovascular events.

A further aim of the invention is to provide a new method for measurement of secretory phospholipase A$_2$ (sPLA$_2$) activity.

Thus, the present invention relates to a method for determining an increased risk of mortality or of a cardiac and/or vascular event in a patient, comprising:

determining the value of sPLA$_2$ activity of said patient as a first risk marker and locating this value in an interval of a set of predetermined intervals of sPLA activity range, determining the value of at least a second risk marker chosen among: CRP level, IgM IC of apoB100 or IgM MDA-LDL level, of said patient and locating this value in an interval of a set of predetermined intervals of CRP level, IgM IC of apoB100 or IgM MDA-LDL level range, assessing the combined intervals obtained with the at least two above mentioned intervals of said patient as a third risk marker, assessing a corresponding odds ratio to said combined intervals and comparing said odds ratio value to predetermined odds ratios according to intervals of sPLA2 activity range and CRP level range, IgM IC of apoB100 or IgM MDA-LDL level range, said predetermined odds ratios being predictive of an increased risk of mortality or of a cardiac and/or vascular event in a patient.

The term IgM IC of apoB100 refers to an antibody (IgM type) immune complex directed against type B100 apolipoprotein.

Lipoproteins are large complexes of molecules that transport lipids (primarily triglycerides and cholesterols) through the blood. Apolipoproteins are proteins on the surface of the lipoprotein complex that bind to specific enzymes or transport proteins on the cell membranes.

The term IgM MDA-LDL refers to an antibody (IgM type) directed against malondialdehyde low density lipoprotein.

By "increased risk" it is meant that a patient for whom the odds ratio obtained from the combined intervals is higher than predetermined odds ratios, is more likely to decease or to be afflicted with a cardiac and/or vascular event than an individual for whom the odds ratio obtained from the combined intervals is below said predetermined odds ratios.

According to the invention, the following events are in particular considered as being cardiac and/or vascular events:

myocardial infarction (MI), vascular cerebral accident, hospitalization due to cardiac and/or vascular diseases, and revascularization procedures.

The measure of sPLA2 activity can be performed by a fluorimetric assay according to Radvanyi et al., (1989) *Anal Biochem.* 177:103-9 as modified by Pernas et al., (Pernas et al. *Biochem. Biophys. Res. Commun.* (1991) 178:1298-1305).

According to another aspect of the invention, the measure of sPLA2 activity can also be performed by an improved fluorimetric assay, using an automated fluorimetric measurement, with a small sample volume, a modified substrate/enzyme ratio (10 nmoles/U instead of 50 nmoles/U) and a thermostat ruled at 30° C., providing a higher precision and sensitivity (2.7%≦within batch coefficient of variation (CV)≦3.2% and between batch CV=5.7%) than the previous method (within batch CV<10% and between batch CV<10%) and a substantially shorter time to complete the assay.

In particular, the following assay is used for automated measurement. The 1-hexadecanoyl-2-(1-pyrenedecanoyl)-sn-glycero-3-phosphomethanol sodium salt (Interchim, Montluçon, France) is used as a substrate for sPLA2. The hydrolysis of this substrate by sPLA2 yields 1-pyrenedecanoic acid, which emits fluorescence at 405 nm. Briefly, 1 nmol of fluorescent substrate in 0.2 ml of buffer substrate (10 mM Tris-HCL pH 8.7, 0.1% albumin, 10 mM CaCl$_2$) was automatically distributed in Black Maxisorp microtitration plate (96 wells). Because the self-quenching properties of the substrate, a low fluorescence is firstly recorded (Fmin) in a Fluostar Optima fluorimeter equipped with a stirring device and thermostat ruled at 30° C. The addition of 30 µl (100 U/mL) of bee venom PLA2 (Sigma Chemical Co., France) leads to a rapid hydrolysis of all substrate (100% of hydrolysis) and an increase in fluorescence to a maximal value (Fmax). To determine the sPLA2 activity in unknown blood samples, 30 µl of sera (E) were automatically distributed and added to the substrate mixture. The fluorescence was recorded at one minute (F) and thus, corresponds to an activity of sPLA2 able to hydrolyse 1 nmol of substrate in one minute (Vmax). A two-point procedure was used to measure the corrected fluorescence intensity of each sample and to evaluate the enzymatic activity (expressed in nmol/min/ml). All samples were tested in duplicate.

The activity (A) of the sample (expressed in nmol/ml/min) is given by the following formula:

$$A = \frac{V \max \cdot F}{E \cdot F \max}$$

The hydrolysis of the substrate in the absence of serum is used as negative control and deduced from PLA2 activity. All samples are tested in duplicate.

Unless otherwise mentioned, all the numerical values given herein for serum sPLA2 activity are measured according to the above defined assay for automated measurement.

The phospholipase that can be used to perform the assay is a secretory phospholipase or a phospholipase with a known activity and preferably a bee venom phospholipase.

The CRP levels were measured with a sandwich-type ELISA according a method described in the literature (Bruins et al., *Circulation,* 1997, 96:3542-3548)

The IgM IC of apo B 100 and IgM MDA-LDL levels were measured according the known methods in the literature (Tsimikas et al., *Circulation,* 2004, 110:1406-1412; Tsimikas et al., *J. Am. Coll. Cardiol.,* 2003, 41, 360-370).

The term "odds ratio" for a given marker is given by the following formula:

$$\frac{\text{Number of events in an interval for a given marker}}{\text{Total number of events in the first interval for the marker}}$$

The total number of people must be the same in each interval.

A given population of individuals can be divided into equal parts (or intervals), each containing the same number of individuals. It can be divided for example into two, three, four or five parts, and then the intervals are named respectively median, tertiles, quartiles or quintiles. Therefore, the term interval used here means median, tertile, quartile or quintile.

When it is divided into four parts, the first interval or quartile corresponds to the part of the given population with the lowest sPLA2 activity, or CRP level but the highest IgM IC of apo B 100 or IgM MDA-LDL level; the last quartile corresponds to part of the given population with the highest sPLA2 activity or CRP level but the lowest IgM IC of apo B 100 IgM or MDA-LDL level, the second and third quartiles corresponding to the rest of the population.

From these intervals or quartiles, an odds ratio can be determined for each marker, by a statistical treatment.

From the above mentioned intervals, a combined odds ratio between two or three combined intervals values (sPLA2 and CRP for example) can be determined by the ratio:

$$\text{Combined odds ratio} = \frac{A}{B} \bigg/ \frac{C}{D}$$

Where:
A=Sum of the number of events in a given interval for each marker
B=Total number of individuals in these given intervals
C=Sum of the number of events in the first interval for each marker
D=Total number of individuals in these first intervals The expression "predetermined odds ratio" designates a threshold value above which a plasma or serum sPLA2 activity and a plasma or serum level of at least a second marker chosen among CRP level, Ig M IC of apo B 100 level or IgM MDA-LDL level, is deemed to be significant of a present or future affliction of a patient with a cardiac and/or vascular related event or pathology.

According to a particular embodiment of the above defined method, the second risk marker is CRP level.

According to a particular embodiment of the above defined method, the patient has been diagnosed as being substantially healthy, in particular with respect to atherosclerosis, cardiac and/or vascular related diseases.

By "substantially healthy" is meant that the patient presents no symptom of affliction by a disease, in particular by an atherosclerosis, cardiac and/or vascular related disease. Such diseases comprise in particular: coronary artery diseases (CAD), carotid atherosclerosis, aortic atherosclerosis, iliac or femoral atherosclerosis, vascular aneurysm, vascular calcification, hypertension, heart failure, and diabetes.

According to another particular embodiment of the above defined method, the patient has been diagnosed as presenting one of the following coronary disorders:
asymptomatic coronary artery disease with silent ischemia or without ischemia,
chronic ischemic disorders without myocardial necrosis, such as stable or effort angina pectoris, acute ischemic disorders without myocardial necrosis, such as unstable angina pectoris, ischemic disorders with myocardial necrosis, such as ST segment elevation myocardial infarction or non-ST segment elevation myocardial infarction.

Tissue ischemia is often defined in relative terms and occurs when the needs in oxygen exceed the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24 h electrocardiogram recording.

Stable and effort angina is typically manifested by a chest pain during exercise and slowly recovers at rest. It usually reflects tissue ischemia during exercise.

Unstable angina is either a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

According to a more particular embodiment of the above defined method, the patient has a medical suspicion of the following coronary disorders:

asymptomatic coronary artery disease with silent ischemia or without ischemia, chronic ischemic disorders without myocardial necrosis, such as stable or effort angina pectoris, acute ischemic disorders without myocardial necrosis, such as unstable angina pectoris, ischemic disorders with myocardial necrosis, such as ST segment elevation myocardial infarction or non-ST segment elevation myocardial infarction.

According to another particular embodiment of the above defined method, no onset of ischemic symptoms has been diagnosed in the patient.

Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves).

According to yet another particular embodiment of the above defined method, an onset of ischemic symptoms has been diagnosed in the patient.

In another preferred embodiment of the above defined method the SPLA$_2$ activity measured for the plasma sample of the patient is higher than about 1.8 nmol/ml/min, in particular higher than about 2 nmol/ml/min, more particularly higher than about 2.5 nmol/ml/min, preferably higher than about 2.9 nmol/ml/min, and more preferably higher than 3.3 as determined by fluorimetric assay according to Radvanyi et al. (1989) *Anal Biochem.* 177:103-9 as modified by Pernas et al. and/or the sPLA2 activity measured from serum sample of the patient is higher than 3.74 nmol/ml/min and preferably higher than 4.29 nmol/ml/min and preferably higher than 4.95 nmol/ml/min as determined by an automated fluorimetric measurement as defined above. In a preferred embodiment, of the above defined method sPLA$_2$ activity in a patient is determined by a process based on a fluorimetric assay comprising contacting a biological sample containing said sPLA$_2$ and taken from said patient, with a substrate at a concentration from 1 nM to 15 nM, the serum sample volume being from 5 µl to 50 µl and the substrate volume being from 100 µl to 300 µl, at a temperature range from about 15° C. to about 40° C. and preferably 30° C.

The phospholipase used could be a phospholipase from bee venom or snake venom like Naja venom, preferably bee venom. It could be a recombinant phospholipase from any species.

The assay is described in example 2.

The advantage of this method is the small sample volume of substrate used and the thermostating, providing a higher precision and sensitivity.

Alternatively, a variant of the automated fluorimetric measurement as defined above can be used, which enables to alleviate imprecision which might result from a non-specific increase in fluorescence intensity due to other factors in the sample, thus interfering with the measure of sPLA2 activity. This method only differs from the above-defined automated fluorimetric measurement method in that the following formula is used for determining sPLA2 activity:

$$A = F \cdot s / [(F\max - F\min) \cdot V]$$

wherein:

A represents sPLA2 activity expressed in nmol/min/ml;

s represents the quantity of substrate expressed in nmol (usually 1 nmol in a volume of 200 µl of working solution);

V represents the sample volume expressed in ml (usually from 0.30 to 0.50 ml);

(Fmax−Fmin) represents the difference between the maximal fluorescence signal at the end of the reaction in the presence of PLA2 from bee venom and the negative control;

F represents the initial slope, within linear range, of the curve representing fluorescence emission as a function of time, expressed in min.$^{-1}$.

The variant is described in detail in the following Example 4.

Using this variant, the following quartile limits for sPLA2 activity in plasma samples of a healthy adult population could be determined: quartile 1 corresponds to the part of a population with the lowest sPLA2 activity (less than 1.22 nmole/min/ml), quartile 2 corresponds to values ranging from 1.22 to 1.54 nmole/min/ml, quartile 3 corresponds to values ranging from 1.54 to 1.93 nmole/min/ml and quartile 4 corresponds to the part of the population with the higher sPLA2 activity (more than 1.93 nmole/min/ml).

Thus, in a particularly preferred embodiment of the above defined method, the sPLA$_2$ activity measured for a plasma sample of the patient is higher than 1.22 nmol/ml/min, preferably higher than 1.54 nmol/ml/min and more preferably higher than 1.93 nmol/ml/min, as determined by the variant of the automated fluorimetric measurement as defined above.

In another preferred embodiment of the above defined method, the CRP level in the serum of a patient is higher than 0.70 mg/l, in particular higher than about 1.45 mg/l, more particularly higher than about 2.5 mg/l and more preferably higher than about 3.1 mg/l.

In a preferred embodiment of the above defined method, the predetermined odds ratios values correspond to the ratios obtained from the association between the intervals of sPLA$_2$ activity comprised in the highest three quartiles of the $sPLA_2$ activity range, and the intervals of CRP level range comprised in the highest three quartiles and preferably in the higher half of the CRP level range, in particular in the higher half of the $sPLA_2$ activity range and the higher half of the CRP level range, more particularly in the highest quartile of said $sPLA_2$ range and in the highest quartile of said CRP level range.

As intended above, a given population is divided in four parts or intervals (quartiles), each containing the same number of individuals, the first interval (quartile) corresponding to the part of the given population with the lowest sPLA2 activities or CRP level, the last interval (quartile) corresponding to the part of the given population with the highest sPLA2 activities or CRP level, and the second and third intervals (quartiles) corresponding to the rest of the population between the first and last intervals.

In another preferred embodiment of the above defined method, the odds ratio obtained from the association between the interval of $sPLA_2$ activity of the patient and the interval of CRP level of said patient, is equal to or higher than about 1.37, in particular equal to or higher than about 1.39, more particularly equal to or higher than 1.57 and preferably equal to or higher than about 2.89.

In a preferred embodiment of the above defined method, the odds ratio, obtained from the association between the intervals of $sPLA_2$ activity of the patient and the interval of CRP level of said patient, is equal to or higher than about 1.37, in particular equal to or higher than about 1.39, more particularly equal to or higher than 1.57, more particularly equal to or higher than about 1.63, and more particularly equal to or higher than about 1.94, preferably equal to or higher than about 2.21, more preferably equal to or higher than about 2.25, more preferably equal to or higher than about 2.51 and more preferably equal to or higher than about 2.89.

The odds ratio of the last interval (quartile) of CRP is equal to 1.61 and the odds ratio of the last interval (quartile) of sPLA2 activity is equal to 1.70.

It means that a patient with a value of CRP level comprised in the last interval (quartile) of predetermined intervals of CRP level range has an increased risk of mortality or of a cardiac and/or vascular event of 61% compared to the first interval.

This same patient with a value of sPLA2 activity comprised in the last interval (quartile) of predetermined intervals of sPLA2 activity range has an increased risk of mortality or of a cardiac and/or vascular event of 70% compared to the first interval.

When the odds ratio value for this same patient, determined with the two above mentioned intervals is compared to predetermined odds ratios according to intervals of sPLA2 activity range and CRP level (equal to 2.89), it indicates that his/her risk of mortality or of a cardiac and/or vascular event is increased by 189%, providing a very better information on the prediction of absolute CAD risk than either biomarker alone (Table 3 and 4).

This improved information was not at all obvious, from the determination or knowledge of each marker taken alone.

In another particularly preferred embodiment of the above defined method, the sPLA2 activity is measured in a biological sample, in particular a serum or a plasma sample, and more particularly a serum sample.

The present invention also relates to an in vitro or ex vivo method for the diagnosis of cardiac and/or vascular diseases in a patient, comprising:
  determining the value of $sPLA_2$ activity of said patient as a first risk marker and locating this value in an interval of a set of predetermined intervals of sPLA activity range,
  determining the value of CRP level of said patient as a second risk marker and locating this value in an interval of a set of predetermined intervals of CRP level range,
  assessing the combined intervals obtained with the at least two above mentioned intervals of said patient as a third risk marker, assessing a corresponding odds ratio to said combined intervals and comparing said odds ratio value to predetermined odds ratios according to intervals of sPLA2 activity range and CRP level range, said predetermined odds ratios being predictive of an increased risk of mortality or of a cardiac and/or vascular event in a patient.

By cardiac and/or vascular diseases are intended afflictions such as: coronary artery disease (CAD), hypertension, atherosclerosis, iliac or femoral atherosclerosis, vascular aneurysm, vascular calcification, hypertension, heart failure, and diabetes.

In a particular embodiment of the above defined in vitro or ex vivo method, a higher odds ratio of a patient as compared to a predetermined odds ratio is indicative of the affliction of said patient with a cardiac and/or vascular disease at the time the determination of the value of sPLA2 activity and the value of CRP level of said patient is made, or is indicative of a future affliction of said patient with a cardiac and/or vascular disease, in particular more than 72 hours after the time determinations respectively of the value of sPLA2 activity and the value of CRP level of said patient are made.

By "future affliction" is meant an affliction the onset of which occurs after the moment when the determination of the odds ratio of said patient has been made.

In another particular embodiment of the above defined in vitro or ex vivo method, the odds ratio between the value of $sPLA_2$ activity of the patient and the value of CRP level of said patient, is equal to or higher than about 1.37, in particular equal to or higher than about 1.39, more particularly equal to or higher than 1.57 and preferably equal to or higher than about 2.89.

In a preferred embodiment of the above defined in vitro or ex vivo method, the odds ratio, between the value of $sPLA_2$ activity of the patient and the value of CRP level of said patient, is equal to or higher than about 1.37, in particular equal to or higher than about 1.39, more particularly equal to or higher than 1.57, more particularly equal to or higher than about 1.63, and more particularly equal to or higher than about 1.94, preferably equal to or higher than about 2.21, more preferably equal to or higher than about 2.25, more preferably equal to or higher than about 2.51 and more preferably equal to or higher than about 2.89.

In another particular embodiment of the above defined in vitro or ex vivo method, the $sPLA_2$ activity and CRP level are measured in a biological sample, in particular a serum sample or a plasma sample, and more particularly a serum sample.

The present invention also relates to the use of means for measuring the $sPLA_2$ activity, and CRP level for the manufacture of a kit intended for determining an increased risk of mortality or of a cardiac and/or vascular event.

The invention also relates to the use of means for measuring the $sPLA_2$ activity, and CRP level for the manufacture of a kit intended for the diagnosis of cardiac and/or vascular diseases.

According to a preferred embodiment of the above defined uses, the means for measuring the $sPLA_2$ activity comprise a compound liable to be hydrolyzed by $sPLA_2$, the hydrolytic products of which can be directly or indirectly quantified and means for measuring CRP level comprise a monoclonal antibody specific to CRP, an enzyme-conjugated antibody specific for CRP, and a substrate for the enzyme, the colour change of the medium being liable to directly or indirectly quantify the CRP level.

The compound liable to be hydrolyzed by sPLA2 is a natural or non natural substrate of the enzyme. In case the hydrolysis products are not quantifiable by themselves, compounds which can react with these products and which yield quantifiable compounds can be used, such a method is an indirect quantification.

The means for measuring CRP levels are those known from the person skilled in the art, for example a high sensitivity CRP, comprising a polyclonal or monoclonal antibody specific to CRP, an enzyme-conjugated antibody specific for CRP, in particular a horseradish peroxidase and a substrate for the enzyme, in particular for the horseradish peroxidase, the colour change of the medium being liable to directly or indirectly quantify the CRP level.

More particularly, in the above defined uses, the compound liable to be hydrolyzed by sPLA2 is a phospholipid or a phospholipid analogue comprising a fluorogenic or a chromogenic moiety.

In a preferred embodiment the phospholipids is a glycerophospholipid which is substituted in position 2 by a fluorescent acyl; such a glycerophospholipid can be for example 1-hexadecanoyl-2-(1-pyrenedecanoyl)-sn-glycero-3-phosphomethanol, and the fluorescent acyl 1-pyrenedecanoyl, and the substrate for horseradish peroxidase is 3,3',5,5'tetramethyl-benzidine (TMB).

Other phospholipids which can be used according to the invention comprise the phospholipids liable to be hydrolyzed by sPLA2, such phospholipids are well known to the man skilled in the art.

Fluorescent acyls liable to be used in the invention notably comprise acyls substituted by fluorescent groups well known to the man skilled in the art, such as pyrene, or fluoresceine for instance.

Alternatively radioactive glycerophospholipids can be used in the above defined method, such as glycerophospholipids substituted in position 2 by radioactive acyls, or radioactive phosphatidyl ethanolamine.

The present invention also relates to a kit intended for determining an increased risk of mortality or of a cardiac and/or vascular event, comprising the following elements:
a sPLA$_2$ buffer,
a compound liable to be hydrolyzed by sPLA$_2$, the hydrolytic products of which can be directly or indirectly quantified, such as 1-pyrenedecanoyl,
a control sPLA$_2$ activity sample, and
a CRP buffer,
a monoclonal antibody specific to CRP,
a enzyme-conjugated antibody specific for CRP,
a control CRP level sample,
each element respectively corresponding to sPLA$_2$ and CRP being liable to be in separate or common unit, The comparison of the odds ratio value obtained with the at least two intervals of said patient to predetermined odds ratios according to intervals of sPLA2 activity range and CRP level, being predictive of an increased risk of mortality or of a cardiac and/or vascular event in a patient.

The term "control sPLA$_2$ activity sample" or "control CRP level sample" used here refers to a sample with a known activity.

The invention also relates to a kit intended for diagnosing a cardiac and/or vascular disease, comprising the following elements:
a sPLA$_2$ buffer,
a compound liable to be hydrolyzed by sPLA$_2$, the hydrolytic products of which can be directly or indirectly quantified, such as 1-pyrenedecanoyl,
a control sPLA$_2$ activity sample, and
a CRP buffer
a monoclonal antibody specific to CRP
an enzyme-conjugated antibody specific for CRP
a control CRP level sample
each element, respectively corresponding to sPLA$_2$ and CRP, being liable to be in separate or common unit.

The comparison of the odds ratio value obtained with the two combined intervals of said patient to predetermined odds ratios according to intervals of sPLA2 activity range and CRP level, being predictive of an increased risk of mortality or of a cardiac and/or vascular event in a patient.

The invention further relates to a method for determining the efficacy of a drug administered to an individual for the treatment of a cardiovascular disease comprising:
i) determining the value of sPLA$_2$ activity of said individual prior the administration of said drug and locating this value in an interval of a set of predetermined intervals of sPLA2 activity range,
ii) determining the value of CRP level of said individual prior the administration of said drug and locating this value in an interval of a set of predetermined intervals of CRP level range,
iii) assessing the odds ratio value obtained with the two above mentioned intervals of said individual prior the administration of said drug, said odds ratio being a reference odds ratio when it is higher than the predetermined odds ratio, and representing a predetermined stage of the disease,
iv) determining the sPLA$_2$ activity and the CRP level of said individual to whom the drug has been administered to obtain an odds ratio after administration,
v) comparing the odds ratio obtained after administration with said reference odds ratio, the difference between the odds ratio obtained after administration and the reference odds ratio indicating the evolution of the cardiovascular disease, and thus enabling to determine the degree of efficacy of the drug.

According to another particular embodiment of the above defined method, the second risk marker is IgM IC of apo B 100 level or IgM MDA-LDL.

All that is described below concerning the IgM IC of apo B100 is useful for the IGM MDA-LDL but with different values.

According to a particular embodiment of the above defined method, the patient has been diagnosed as being substantially healthy, in particular with respect to atherosclerosis, cardiac and/or vascular related diseases.

By "substantially healthy" is meant that the patient presents no symptom of affliction by a disease, in particular by an atherosclerosis, cardiac and/or vascular related disease. Such diseases comprise in particular: coronary artery diseases (CAD), carotid atherosclerosis, aortic atherosclerosis, iliac or femoral atherosclerosis, vascular aneurysm, vascular calcification, hypertension, heart failure, and diabetes.

According to another particular embodiment of the above defined method, the patient has been diagnosed as presenting one of the following coronary disorders:

asymptomatic coronary artery disease with silent ischemia or without ischemia, chronic ischemic disorders without myocardial necrosis, such as stable or effort angina pectoris, acute ischemic disorders without myocardial necrosis, such as unstable angina pectoris, ischemic disorders with myocardial necrosis, such as ST segment elevation myocardial infarction or non-ST segment elevation myocardial infarction.

Tissue ischemia is often defined in relative terms and occurs when the needs in oxygen exceed the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24 h electrocardiogram recording.

Stable and effort angina is typically manifested by a chest pain during exercise and slowly recovers at rest. It usually reflects tissue ischemia during exercise.

Unstable angina is either a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

According to a more particular embodiment of the above defined method, the patient has a medical suspicion of the following coronary disorders:

asymptomatic coronary artery disease with silent ischemia or without ischemia, chronic ischemic disorders without myocardial necrosis, such as stable or effort angina pectoris, acute ischemic disorders without myocardial necrosis, such as unstable angina pectoris, ischemic disorders with myocardial necrosis, such as ST segment elevation myocardial infarction or non-ST segment elevation myocardial infarction.

According to another particular embodiment of the above defined method, no onset of ischemic symptoms has been diagnosed in the patient.

Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves).

According to yet another particular embodiment of the above defined method, an onset of ischemic symptoms has been diagnosed in the patient.

In another preferred embodiment of the above defined method the sPLA$_2$ activity of the patient is higher than about 1.8 nmol/ml/min, in particular higher than about 2 nmol/ml/min, more particularly higher than about 2.5 nmol/ml/min, preferably higher than about 2.9 nmol/ml/min, and more preferably higher than 3.3 as determined by fluorimetric assay according to Radvanyi et al. (1989) *Anal Biochem*. 177:103-9 as modified by Pernas et al. and/or the sPLA2 activity measured from serum sample of the patient is higher than 3.74 nmol/ml/min and preferably higher than 4.29 nmol/ml/min and preferably higher than 4.95 nmol/ml/min as determined by an automated fluorimetric measurement.

In a preferred embodiment, of the above defined method sPLA$_2$ activity in a patient is determined by a process based on a fluorimetric assay comprising contacting a biological sample containing said sPLA$_2$ and taken from said patient with a substrate at a concentration from 1 nM to 15 nM, the serum sample volume being from 5 µl to 50 µl and the substrate volume being from 100 µl to 300 µl, at a temperature range from about 15° C. to about 40° C. and preferably 30° C.

Thus, in a particularly preferred embodiment of the above defined method, the sPLA$_2$ activity measured for a plasma sample of the patient is higher than 1.22 nmol/ml/min, preferably higher than 1.54 nmol/ml/min and more preferably higher than 1.93 nmol/ml/min, as determined by the variant of the automated fluorimetric measurement as defined above.

In another preferred embodiment of the above defined method, the IgM of apo B100 level in the plasma of a patient is lower than 2922 RLU, in particular lower than about 2543 RLU, more particularly lower than about 1548 RLU and more preferably lower than about 1373 RLU (Table 5).

The abbreviation RLU means Radio Luminescence (or Light) Unit, used to measure the level of IgM IC of apoB100 (Tsimikas et al., *Circulation*, 2004, 110:1406-1412; Tsimikas et al., *J. Am. Coll. Cardiol.*, 2003, 41, 360-370). (see example 3)

Anti-oxidized LDL antibodies such as IgM IC of apoB100 or IgM IC of MDA-LDL have been found in humans, and the accumulating evidences seem to support the idea that anti-oxidized LDL antibodies have a protective role against atherogenesis (Binder et al., Nat. Med. 2002, 8, 1218-1226). Therefore, in opposition to sPLA2 activity and CRP level, the lower level of IgM IC of apoB100 corresponds to the higher risk of a cardiovascular event.

The assay is described in example 3.

In a preferred embodiment of the above defined method, the predetermined odds ratios values correspond to the ratios obtained from the association between the intervals of sPLA$_2$ activity comprised in the highest three quartiles of the sPLA$_2$ activity range and the intervals of IgM IC of apoB 100 level comprised in the lowest three quartiles of the IgM IC of apoB 100 level range, in particular in the higher half of the sPLA$_2$ activity range and the lower half of the IgM IC of apoB 100 level, more particularly in the highest quartile of said SPLA$_2$ range and in the lowest quartile of said IgM IC of apoB 100 range.

In another preferred embodiment of the above defined method, the odds ratio obtained with the at least two combined intervals of sPLA$_2$ activity of the patient and the interval of IgM IC of apoB 100 level of said patient, is higher than about 1.37, preferably higher than 2.70, more preferably higher than 3.15 and more preferably higher than 4.99.

The odds ratio obtained between the lower median of IgM IC of apoB100 and the highest tertile of sPLA2 is represented in table 6.

In another particularly preferred embodiment of the above defined method, the sPLA$_2$ activity and IgM IC of apoB 100 level are measured in a biological sample, in particular a serum sample or a plasma sample, and more particularly a plasma sample.

The present invention also relates to an in vitro or ex vivo method for the diagnosis of cardiac and/or vascular diseases in a patient, comprising:
- determining the value of sPLA$_2$ activity of said patient as a first risk marker and locating this value in an interval of a set of predetermined intervals of sPLA activity range,
- determining the value of IgM IC of apoB100 of said patient as a second risk marker and locating this value in an interval of a set of predetermined intervals IgM IC of apoB100 range,
- assessing the odds ratio value obtained with the at least two above mentioned intervals of said patient as a third risk marker and comparing said odds ratio value to predetermined odds ratios according to intervals of sPLA2 activity range and IgM IC of apoB100, said predetermined odds ratio being predictive of an increased risk of mortality or of a cardiac and/or vascular event in a patient.

By cardiac and/or vascular diseases are intended afflictions such as: coronary artery disease (CAD), hypertension, atherosclerosis, iliac or femoral atherosclerosis, vascular aneurysm, vascular calcification, hypertension, heart failure, and diabetes.

In a particular embodiment of the above defined in vitro or ex vivo method, a higher odds ratio of combined intervals of a patient as compared to a predetermined odds ratio is indicative of the affliction of said patient with a cardiac and/or vascular disease at the time the determination of the value of sPLA2 activity and the value of IgM IC of apoB 100 level of said patient is made, or is indicative of a future affliction of said patient with a cardiac and/or vascular disease, in particular more than 72 hours after the time the determinations respectively of the value of sPLA2 activity and the value of IgM IC of apoB 100 level of said patient are made.

By "future affliction" is meant an affliction the onset of which occurs after the moment when the determination of the sPLA2 activity of said patient has been made.

In another particular embodiment of the above defined in vitro or ex vivo method, the odds ratio value obtained with the at least two combined intervals of sPLA$_2$ activity of the patient and the value of IgM IC of apoB 100 level of said patient, is higher than about 1.37, preferably higher than 2.70, more preferably higher than 3.15 and more preferably higher than 4.99.

In another particular embodiment of the above defined in vitro or ex vivo method, the sPLA$_2$ activity and IgM IC of apoB 100 level are measured in a biological sample, in particular a serum sample or a plasma sample, and more particularly a plasma sample.

The present invention also relates to the use of means for measuring the sPLA$_2$ activity, and IgM IC of apoB 100 level for the manufacture of a kit intended for determining an increased risk of mortality or of a cardiac and/or vascular event.

The invention also relates to the use of means for measuring the SPLA$_2$ activity, and IgM IC of apoB 100 level for the manufacture of a kit intended for the diagnosis of a cardiac and/or vascular diseases.

According to a preferred embodiment of the above defined uses, the means for measuring the sPLA$_2$ activity comprise a compound liable to be hydrolyzed by sPLA$_2$, the hydrolytic products of which can be directly or indirectly quantified and means for measuring IgM IC of apoB 100 level comprise a specific monoclonal antibody, a labelled anti-human IgM and a chemiluminescent reagent.

The compound liable to be hydrolyzed by sPLA2 is a natural or non natural substrate of the enzyme. In case the hydrolysis products are not quantifiable by themselves, compounds which can react with these products and which yield quantifiable compounds can be used; such a method is an indirect quantification.

More particularly, in the above defined uses, the compound liable to be hydrolyzed by sPLA2 is a phospholipid or a phospholipid analogue comprising a fluorogenic or a chromogenic moiety.

In a preferred embodiment the phospholipids is a glycerophospholipid which is substituted in position 2 by a fluorescent acyl; such a glycerophospholipid can be for example 1-hexadecanoyl-2-(1-pyrenedecanoyl)-sn-glycero-3-phosphomethanol, and the fluorescent acyl 1-pyrenedecanoyl.

Other phospholipids which can be used according to the invention comprise the phospholipids liable to be hydrolyzed by sPLA2, such phospholipids are well known to the man skilled in the art.

Fluorescent acyls liable to be used in the invention notably comprise acyls substituted by fluorescent groups well known to the man skilled in the art, such as pyrene, ou fluoresceine for instance.

Alternatively radioactive glycerophospholipids can be used in the above defined method, such as glycerophospholipids substituted in position 2 by radioactive acyls, or radioactive phosphatidyl ethanolamine.

The specific monoclonal antibody is for example MB47.

The labelled anti-human IgM is for example alkaline phosphatase-labeled goat anti-human IgM.

The chemiluminescent reagent is a substrate for alkaline phosphatase, for example LumiPhos 530 (Lumigen, Inc).

The present invention also relates to a kit intended for
- determining an increased risk of mortality or of a cardiac and/or vascular event, comprising the following elements:
  - a sPLA$_2$ buffer,
  - a compound liable to be hydrolyzed by sPLA$_2$, the hydrolytic products of which can be directly or indirectly quantified, such as 1-pyrenedecanoyl,
  - a control sPLA$_2$ activity sample, and
  - an IgM of apo B100 buffer,
  - a monoclonal antibody specific for human apo B 100,
  - a alkaline phosphatase labelled anti human IgM,
  - a control IgM IC of apoB 100 level sample,
  - each elements respectively corresponding to sPLA$_2$ and IgM IC of apoB 100 being liable to be in separate or common unit.

A chemiluminescent reagent for example LumiPhos 530 is added to read the plates in a chemiluminometer.

The term "control sPLA$_2$ activity sample" or "control IgM IC of apo B100 level sample" used here refers to a sample with a known activity.

The comparison of the odds ratio value obtained with the two combined intervals of said patient to predetermined odds ratios according to intervals of sPLA2 activity range and IgM IC of apoB100 range, being predictive of an increased risk of mortality or of a cardiac and/or vascular event in a patient.

The invention also relates to a kit intended for diagnosing a cardiac and/or vascular disease, comprising the following elements:
  a sPLA$_2$ buffer,
  a compound liable to be hydrolyzed by sPLA$_2$, the hydrolytic products of which can be directly or indirectly quantified, such as 1-pyrenedecanoyl,
  a control sPLA$_2$ activity sample, and
  an IgM of apo B100 buffer
  a monoclonal antibody specific for human apo B 100
  an alkaline phosphatase labelled anti human IgM
  a control IgM IC of apoB 100 level sample each elements respectively corresponding to $sPLA_2$ and IgM IC of apoB 100 being liable to be in separate or common unit, A chemiluminescent reagent for example LumiPhos 530 is added to read the plates in a chemiluminometer.

The comparison of the odds ratio value obtained with the two combined intervals of said patient to predetermined odds ratios according to intervals of sPLA2 activity range and IgM IC of apoB100 range, being predictive of an increased risk of mortality or of a cardiac and/or vascular event in a patient.

The invention further relates to a method for determining the efficacy of a drug administered to an individual for the treatment of a cardiovascular disease comprising:
  i) determining the value of $sPLA_2$ activity of said individual prior the administration of said drug and locating this value in an interval of a set of predetermined intervals of sPLA activity range
  ii) determining the value of IgM IC of apoB100 level of said individual prior the administration of said drug and locating this value in an interval of a set of predetermined intervals of IgM IC of apoB100 level range.
  iii) assessing the odds ratio value obtained with the two combined above mentioned intervals of said individual prior the administration of said drug, said odds ratio being a reference odds ratio when it is higher than the predetermined odds ratio, and representing a predetermined stage of the disease,
  iv) determining the $sPLA_2$ activity and the IgM IC of apoB100 level of said individual to whom the drug has been administered to obtain an odds ratio after administration,
  v) comparing the odds ratio obtained after administration with said reference odds ratio, the difference between the odds ratio obtained after administration and the reference odds ratio indicating the evolution of the cardiovascular disease, and thus enabling to determine the degree of efficacy of the drug.

According to a particular embodiment of the above defined method, the second risk marker is CRP level and IgM IC of apoB 100 level or IgM MDA-LDL.

According to a particular embodiment of the above defined method, the patient has been diagnosed as being substantially healthy, in particular with respect to atherosclerosis, cardiac and/or vascular related diseases.

By "substantially healthy" is meant that the patient presents no symptom of affliction by a disease, in particular by an atherosclerosis, cardiac and/or vascular related disease. Such diseases comprise in particular: coronary artery diseases (CAD), carotid atherosclerosis, aortic atherosclerosis, iliac or femoral atherosclerosis, vascular aneurysm, vascular calcification, hypertension, heart failure, and diabetes.

According to another particular embodiment of the above defined method, the patient has been diagnosed as presenting one of the following coronary disorders:
  asymptomatic coronary artery disease with silent ischemia or without ischemia,
  chronic ischemic disorders without myocardial necrosis, such as stable or effort angina pectoris,
  acute ischemic disorders without myocardial necrosis, such as unstable angina pectoris,
  ischemic disorders with myocardial necrosis, such as ST segment elevation myocardial infarction or non-ST segment elevation myocardial infarction.

Tissue ischemia is often defined in relative terms and occurs when the needs in oxygen exceed the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24 h electrocardiogram recording.

Stable and effort angina is typically manifested by a chest pain during exercise and slowly recovers at rest. It usually reflects tissue ischemia during exercise.

Unstable angina is either a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

According to a more particular embodiment of the above defined method, the patient has a medical suspicion of the following coronary disorders:
  asymptomatic coronary artery disease with silent ischemia or without ischemia,
  chronic ischemic disorders without myocardial necrosis, such as stable or effort angina pectoris,
  acute ischemic disorders without myocardial necrosis, such as unstable angina pectoris,
  ischemic disorders with myocardial necrosis, such as ST segment elevation myocardial infarction or non-ST segment elevation myocardial infarction.

According to another particular embodiment of the above defined method, no onset of ischemic symptoms has been diagnosed in the patient.

Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves).

According to yet another particular embodiment of the above defined method, an onset of ischemic symptoms has been diagnosed in the patient.

In another preferred embodiment of the above defined method the $sPLA_2$ activity of the patient is higher than about 1.8 nmol/ml/min, in particular higher than about 2 nmol/ml/min, more particularly higher than about 2.5 nmol/ml/min, preferably higher than about 2.9 nmol/ml/min, and more preferably higher than 3.3 as determined by fluorimetric assay according to Radvanyi et al. (1989) *Anal Biochem.* 177:103-9 as modified by Pernas et al. and/or the sPLA2 activity measured from serum sample of the patient is higher than 3.74 nmol/ml/min and preferably higher than 4.29 nmol/ml/min and preferably higher than 4.95 nmol/ml/min as determined by an automated fluorimetric measurement.

In a preferred embodiment, of the above defined method the sPLA2 activity in a patient is determined by a process based on a fluorimetric assay comprising contacting a biological sample containing said $sPLA_2$ and taken from said patient with a substrate at a concentration from 1 nM to 15 nM, the serum sample volume being from 5 µl to 50 µl and the substrate volume being from 100 µl to 300 µl, at a temperature range from about 15° C. to about 40° C. and preferably 30° C.

Thus, in a particularly preferred embodiment of the above defined method, the sPLA$_2$ activity measured for a plasma sample of the patient is higher than 1.22 nmol/ml/min, preferably higher than 1.54 nmol/ml/min and more preferably higher than 1.93 nmol/ml/min, as determined by the variant of the automated fluorimetric measurement as defined above.

In another preferred embodiment of the above defined method the CRP level in the serum of a patient is higher than 0.70 mg/l, in particular higher than about 1.45 mg/l, more particularly higher than about 2.5 mg/l and more preferably higher than about 3.1 mg/l In another preferred embodiment of the above defined method the IgM of apo B100 level in the plasma of a patient is lower than 2922 RLU, in particular lower than about 2543 RLU, more particularly lower than about 1548 RLU and more preferably lower than about 1373 RLU.

As defined above, the abbreviation RLU means Radio Luminescence Unit, used to measure the level of IgM IC of apoB100 (see example 3)

In a preferred embodiment of the above defined method, the predetermined odds ratios values correspond to the ratios obtained from the association between:
the intervals of sPLA$_2$ activity comprised in the highest three quartiles of the sPLA$_2$ activity range,
the intervals of CRP level comprised in the highest three quartiles of the CRP level range, and
the intervals of IgM IC of apoB 100 level comprised in the lowest three quartiles of the IgM IC of apoB 100 level range,
in particular in the higher half of the sPLA$_2$ activity range, the higher half of the CRP level range and the lower half of the IgM IC of apoB 100 level range, and more particularly in the highest quartile of said sPLA$_2$ range, in the highest quartile of said CRP level range, and in the lowest quartile of said IgM IC of apoB 100 range.

In another particularly preferred embodiment of the above defined method, the sPLA$_2$ activity, CRP level, and IgM IC of apoB 100 or IgM MDA-LDL are measured in a biological sample, in particular a serum sample or a plasma sample, and more particularly a serum sample.

The present invention also relates to an in vitro or ex vivo method for the diagnosis of cardiac and/or vascular diseases in a patient, comprising:
determining the value of sPLA$_2$ activity of said patient and locating this value in an interval of a set of predetermined intervals of sPLA activity range,
determining the value of CRP level of said patient and locating this value in an interval of a set of predetermined intervals of CRP level range,
determining the value of IgM IC of apoB100 of said patient marker and locating this value in an interval of a set of predetermined intervals IgM IC of apoB100 range,
assessing the combined intervals obtained with the three above mentioned intervals of said patient, assessing a corresponding odds ratio to said combined intervals and comparing said odds ratio value to predetermined odds ratios according to intervals of sPLA2 activity range, CRP level range and IgM IC of apoB100 level range, said predetermined odds ratio being predictive of an increased risk of mortality or of a cardiac and/or vascular event in a patient.

By cardiac and/or vascular diseases are intended afflictions such as: coronary artery disease (CAD), hypertension, atherosclerosis, iliac or femoral atherosclerosis, vascular aneurysm, vascular calcification, hypertension, heart failure, and diabetes.

In a particular embodiment of the above defined in vitro or ex vivo method, a higher odds ratio of a patient as compared to a predetermined odds ratio is indicative of the affliction of said patient with a cardiac and/or vascular disease at the time the determination of the value of sPLA2 activity, the value of CRP level, and, the value of IgM IC of apoB 100 level of said patient is made, or is indicative of a future affliction of said patient with a cardiac and/or vascular disease, in particular more than 72 hours after the time the determinations respectively of the value of sPLA2 activity, the value of CRP level, and the value of IgM IC of apoB 100 level of said patient are made.

By "future affliction" is meant an affliction the onset of which occurs after the moment when the determination of the odds ratio of said patient has been made.

In another particular embodiment of the above defined in vitro or ex vivo method, the sPLA$_2$ activity and CRP level and, the value of IgM IC of apoB 100 level are measured in a biological sample, in particular a serum sample or a plasma sample, and more particularly a serum sample.

The present invention also relates to the use of means for measuring the sPLA$_2$ activity, CRP level and IgM IC of apoB 100 level for the manufacture of a kit intended for the diagnosis of a cardiac and/or vascular diseases.

The invention also relates to the use of means for measuring the SPLA$_2$ activity, CRP level and IgM IC of apoB 100 level for the manufacture of a kit intended for the diagnosis of a cardiac and/or vascular diseases.

According to a preferred embodiment of the above defined uses, the means for measuring the sPLA$_2$ activity comprise a compound liable to be hydrolyzed by sPLA$_2$, the hydrolytic products of which can be directly or indirectly quantified, means for measuring CRP level comprise a monoclonal antibody specific to CRP, an enzyme-conjugated antibody specific for CRP, and a substrate for the enzyme, the colour change of the medium being liable to directly or indirectly quantify the CRP level and the means for measuring IgM IC of apoB 100 level comprise a monoclonal antibody specific, a labelled anti-human IgM and a chemiluminescent reagent.

The compound liable to be hydrolyzed by sPLA2 is a natural or non natural substrate of the enzyme. In case the hydrolysis products are not quantifiable by themselves, compounds which can react with these products and which yield quantifiable compounds can be used; such a method is an indirect quantification.

More particularly, in the above defined uses, the compound liable to be hydrolyzed by sPLA$_2$ is a phospholipid or a phospholipid analogue comprising a fluorogenic or a chromogenic moiety, and the monoclonal antibody is specific for human apo B 100 and the anti human IgM is the alkaline phosphatase-labelled anti IgM.

In a preferred embodiment the phospholipids is a glycerophospholipid which is substituted in position 2 by a fluorescent acyl; such a glycerophospholipid can be for example 1-hexadecanoyl-2-(1-pyrenedecanoyl)-sn-glycero-3-phosphomethanol, and the fluorescent acyl 1-pyrenedecanoyl, and the substrate for horseradish peroxidase is 3,3',5,5'tetramethyl-benzidine (TMB).

Other phospholipids which can be used according to the invention comprise the phospholipids liable to be hydrolyzed by sPLA2, such phospholipids are well known to the man skilled in the art.

Fluorescent acyls liable to be used in the invention notably comprise acyls substituted by fluorescent groups well known to the man skilled in the art, such as pyrene, ou fluoresceine for instance.

Alternatively radioactive glycerophospholipids can be used in the above defined method, such as glycerophospholipids substituted in position 2 by radioactive acyls, or radioactive phosphatidyl ethanolamine.

The present invention also relates to a kit intended for determining an increased risk of mortality or of a cardiac and/or vascular event, comprising the following elements:
a $sPLA_2$ buffer,
a compound liable to be hydrolyzed by $sPLA_2$, the hydrolytic products of which can be directly or indirectly quantified, such as 1-pyrenedecanoyl,
a control $sPLA_2$ activity sample, and
a CRP buffer
a monoclonal antibody specific to CRP
an enzyme-conjugated antibody specific for CRP
a control CRP level sample and
an IgM of apo B100 buffer
a chemiluminescent reagent
a monoclonal antibody specific for human apo B 100
a alkaline phosphatase labelled anti human IgM
a control IgM IC of apoB 100 level sample
each element respectively corresponding to $sPLA_2$, CRP and IgM IC of apoB 100 being liable to be in separate or common unit, The comparison of the odds ratio value obtained with the three intervals of said patient to predetermined odds ratios according to intervals of sPLA2 activity range, CRP level range and IgM IC of apoB100 range, being predictive of an increased risk of mortality or of a cardiac and/or vascular event in a patient.

The invention further relates to a method for determining the efficacy of a drug administered to an individual for the treatment of a cardiovascular disease comprising:
i) determining the value of $sPLA_2$ activity of said individual prior the administration of said drug and locating this value in an interval of a set of predetermined intervals of sPLA activity range,
ii) determining the value of CRP level of said individual prior the administration of said drug and locating this value in an interval of a set of predetermined intervals of CRP level range,
iii) determining the value of IgM IC of apoB100 level of said individual prior the administration of said drug and locating this value in an interval of a set of predetermined intervals of IgM IC of apoB100 level range,
iv) assessing the odds ratio value obtained with the three intervals of said individual prior the administration of said drug, said odds ratio being a reference odds ratio when it is higher than the predetermined odds ratio, and representing a predetermined stage of the disease,
v) determining the $sPLA_2$ activity and the CRP level, and the IgM IC of apoB100 level of said individual to whom the drug has been administered to obtain an odds ratio after administration,
vi) comparing the odds ratio obtained after administration with said reference odds ratio, the difference between the odds ratio obtained after administration and the reference odds ratio indicating the evolution of the cardiovascular disease, and thus enabling to determine the degree of efficacy of the drug.

The invention also relates to a process for determining phospholipase activity in a patient based on a fluorimetric assay comprising contacting a biological sample containing phospholipase preferably isolated from bee venom, taken from said patient with a substrate at a concentration from 1 nM to 15 nM, the serum sample volume being from 5 µl to 50 µl and the substrate volume being from 100 µl to 300 µl, at a temperature range from about 15° C. to about 40° C. and preferably 30° C.

The phospholipase that can be used to perform the assay is a secretory phospholipase or a phospholipase with a known activity from bee venom or snake venom like Naja venom, preferably bee venom. It could be a recombinant phospholipase from any species.

According to a preferred embodiment of the above defined process, the sPLA2 activity is determined in a patient.

The present invention also relates to a method for determining an increased risk of mortality or of a cardiac and/or vascular event in a patient, comprising:
determining the sPLA2 activity of said patient,
comparing said activity to a predetermined value,
a higher sPLA2 activity of said patient as compared to said predetermined value being indicative of an increased risk of mortality or of a cardiac and/or vascular event.

By "increased risk" it is meant that a patient for whom the sPLA2 activity is higher than the predetermined value is more likely to decease or to be afflicted with a cardiac and/or vascular event than an individual for whom the sPLA2 activity is below said predetermined value.

According to the invention, the following events are in particular considered as being cardiac and/or vascular events: myocardial infarction (MI), vascular cerebral accident, hospitalization due to cardiac and/or vascular diseases, and revascularization procedures.

According to a particular embodiment of the above defined method, the patient has been diagnosed as being substantially healthy, in particular with respect to atherosclerosis, cardiac and/or vascular related diseases.

By "substantially healthy" is meant that the patient presents no symptom of affliction by a disease, in particular by an atherosclerosis, cardiac and/or vascular related disease. Such diseases comprise in particular: coronary artery diseases (CAD), carotid atherosclerosis, aortic atherosclerosis, iliac or femoral atherosclerosis, vascular aneurysm, vascular calcification, hypertension, heart failure, and diabetes.

According to another particular embodiment of the above defined method, the patient has been diagnosed as presenting one of the following coronary disorders:
asymptomatic coronary artery disease with silent ischemia or without ischemia,
chronic ischemic disorders without myocardial necrosis, such as stable or effort angina pectoris,
acute ischemic disorders without myocardial necrosis, such as unstable angina pectoris,
ischemic disorders with myocardial necrosis, such as ST segment elevation myocardial infarction or non-ST segment elevation myocardial infarction.

Tissue ischemia is often defined in relative terms and occurs when the needs in oxygen exceed the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24 h electrocardiogram recording.

Stable and effort angina is typically manifested by a chest pain during exercise and slowly recovers at rest. It usually reflects tissue ischemia during exercise.

Unstable angina is either a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

According to a more particular embodiment of the above defined method, the patient has a medical suspicion of the following coronary disorders:

asymptomatic coronary artery disease with silent ischemia or without ischemia, chronic ischemic disorders without myocardial necrosis, such as stable or effort angina pectoris, acute ischemic disorders without myocardial necrosis, such as unstable angina pectoris, ischemic disorders with myocardial necrosis, such as ST segment elevation myocardial infarction or non-ST segment elevation myocardial infarction.

According to another particular embodiment of the above defined method, no onset of ischemic symptoms has been diagnosed in the patient.

Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves).

According to yet another particular embodiment of the above defined method, an onset of ischemic symptoms has been diagnosed in the patient.

In a preferred embodiment of the above defined method, the predetermined value corresponds to a $sPLA_2$ activity comprised in the highest three quartiles of the $sPLA_2$ activity range of a substantially healthy individual, in particular in the higher half, more particularly in the highest quartile of said range.

As intended above, a given population of substantially healthy individuals is divided in four parts (or quartiles), each containing the same number of individuals, the first quartile corresponding to the part of the given population with the lowest sPLA2 activities, the last quartile corresponding to the part of the given population with the highest sPLA2 activities, and the second and third quartiles corresponding to the rest of the population between the first and last quartiles.

In a preferred embodiment of the above defined method, the $SPLA_2$ activity of the patient is higher than about 3.74 nmol/ml/min, in particular higher than about 4.29 nmol/ml/min, more particularly higher than about 4.95 nmol/ml/min.

In another particularly preferred embodiment of the above defined method, the sPLA2 activity is measured in a biological sample, in particular a serum sample.

The invention further relates to a method for screening drugs liable to be used for the manufacture of medicaments intended for the prevention or the treatment of cardiac and/or vascular pathologies, characterized in that:

in a first step the sPLA2 activity of a test animal, constitutively presenting a higher sPLA2 activity with respect to substantially healthy animals of the same species and to which a drug to be screened has been administered, is measured in vitro, in a second step, the measured activity is compared to the sPLA2 activity of said test animal prior to the administration of said drug to be screened, in a third step, the screened drug is selected if the measured activity is lower than the sPLA2 activity of the test animal prior to the administration of said drug to be screened.

In a preferred embodiment of the above defined screening method, the test animal is a non-human transgenic animal such as a mouse or a rat.

In another preferred embodiment of the above defined screening method the sPLA2 activity is measured from plasma samples of the test animal.

In yet another preferred embodiment of the above defined screening method, the animal is sacrificed after the sPLA2 activity has been measured.

DESCRIPTION OF THE FIGURES

FIG. 1

This figure shows the linearity of the measurement method between 0 and 100 U/ml of sPLA2.

FIG. 2

Patients with a level of IgM IC of apoB100 located in the lower median (<1909, see table 4) and an activity of sPLA2 located in the highest tertile (>2.9 nmol/ml/min) have an increased risk of mortality. After 300 days, their survival distribution function without infarction is lower than 0.75. That means less than 75% of individuals survived without myocardial infarction.

EXAMPLES

Example 1

Circulating Secretory Phospholipase A2 Activity and Risk of Incident Coronary Events in Healthy Men and Women, the Epic-Norfolk Study Methods Detailed description of the European Prospective Investigation Into Cancer and Nutrition (EPIC-Norfolk) follow-up study have been published previously (Day N. et al., *Br. J. Cancer,* 1999; 80 Suppl. I: 95-103. Briefly, this prospective population study of 25,663 men and women recruited from age-sex registers of general practices in Norfolk, aged between 45 and 79 years, was designed to investigate dietary and other determinants of cancer. The participants completed a baseline questionnaire survey between 1993 and 1997, attended a clinic visit and were followed up to November 2003, an average of about 6 years. All individuals have been flagged for death certification at the UK Office of National Statistics, with vital status ascertained for the entire cohort. In addition, participants admitted to hospital were identified using their unique National Health Service number by data linkage with the East Norfolk Health Authority database, which identifies all hospital contacts throughout England and Wales for Norfolk residents. The study was approved by the Norwich Health Authority Ethics Committee, and all participants provided written informed consent Study Population A nested-case control study was performed among participants in the Epic-Norfolk study. Case ascertainment has been described in detail elsewhere (Boekholdt, S. M., *Circulation*, 2004; 110:1418-1423. Shortly, cases were those individuals who were identified as having fatal or non fatal CAD during follow-up. CAD was defined as codes 410-414 according to the International Classification of Diseases 9th revision. Were excluded all individuals who reported a history of heart attack or stroke at the baseline clinic visit.

Controls were study participants who remained free of any cardiovascular disease during follow-up. Two controls to each case by sex, age (within 5 years) and time of enrolment (within 3 months) were matched.

Study Measurements

Blood samples were stored at −80° C. at the Department of Clinical Biochemistry, University of Cambridge. Serum levels of total cholesterol, HDL-cholesterol (HDL-C) and triglycerides were measured on fresh samples with the RA 1000 (Bayer Diagnostics, Basingstoke, UK), and LDL-cholesterol (LDL-C) levels were calculated with the Friedewald formula (Friedewald W. T. et al., *Clin Chem.* 1972; 18:499-502. CRP levels were measured with a sandwich-type ELISA as previously described (Bruins P. et al. *Circulation.* 1997; 96:3542-3548).

Serum sPLA2 activity was measured by a selective fluorimetric assay of Radvanyi et al. (*Anal Biochem.* 1989; 177: 103-109), as modified by Pernas et al. (*Biophys Res Commun.* 1991; 178:1298-1305). The sPLA2 activity was measured using fluorescent substrate 1-hexadecanoyl-2-(1-pyrenedecanoyl)-sn-glycero-3 phosphomethanol, sodium salt (Interchim, Montluçon, France) as previously described (Mallat Z. et al. *J Am Coll Cardiol.* 2005; 46:1249-1257). One hundred percent hydrolysis of the fluorescent substrate was measured using 0.1 unit PLA2 from Bee venom (Sigma Chemical Co., France). The hydrolysis of substrate in the absence of plasma was used as negative control and deduced from PLA2 activity. All the samples were tested in duplicate and plasma activity was expressed as nmole/min/ml. The minimum detectable activity was 0.10 nmole/min/ml. The imprecision of sPLA2 activity fluorimetric assay was determined by measurement of samples with low (1.25 nmol/min/ml) and high (9.5 nmol/min/ml) sPLA2 activity. Within-batch CVs ranged from 2.7% (low-activity sample) to 3.2% (high-activity sample) and the between-batch CV was 5.7%.

All the samples were analyzed in random order to avoid systemic bias. Researchers and laboratory personnel were blinded to identifiable information, and could identify samples by number only.

Statistical Analysis

Baseline characteristics were compared between cases and matched controls taking into account the matching between them. A mixed effect model was used for continuous variables and conditional logistic regression was used for categorical variables. Because triglycerides, CRP, sPLA2 antigen levels and sPLA2 activity had a skewed distribution, values were log-transformed before being used as continuous variables in statistical analyses; however, in the tables, untransformed medians and corresponding interquartile ranges are shown. To determine relationships between plasma sPLA2 activity and traditional cardiovascular risk factors, mean risk factor levels per sPLA2 activity quartile were calculated.

Quartiles were based on the distribution in the controls. For sex-specific analyses, sex-specific quartiles were used, and for pooled analyses, quartiles based on the sexes combined were used.

In addition, Pearson correlation coefficients were calculated to assess the relationship between sPLA2 activity as a continuous variable and other continuous biomarkers of risk.

Odds ratios and corresponding 95% confidence intervals (95% CIs) as an estimate of the relative risk of incident CAD were calculated using conditional logistic regression analysis. The lowest sPLA2 activity quartile was used as reference category.

Odds Ratios were adjusted for the following cardiovascular risk factors: body mass index, diabetes, systolic blood pressure, LDL-C, HDL-C, and smoking (never, previous, current).

Odds Ratios were also calculated after additional adjustment for CRP levels and serum levels of sPLA2 type IIA concentration. The trend across the quartiles of sPLA2 activity and CRP was tested by entering a single ordinal term for the quartile in the logistic regression model. The deviation from linearity was tested by comparing models containing quartile indicators with those containing a linear term in a likelihood-ratio test with 2 degrees of freedom (df).

Furthermore, the additional prognostic contribution of quartiles of sPLA2 activity to models containing the other variable, with a likelihood-ratio test, was also tested. To assess whether sPLA2 activity levels had predictive value on top of the Framingham Risk Score, odds ratios for future CAD per sPLA2 activity quartile were calculated, simultaneously adjusting for the Framingham Risk Score as a continuous variable. The Framingham Risk Score was calculated using a previously reported algorithm, which takes into account age, sex, total cholesterol, HDL-C, systolic and diastolic blood pressure, smoking and the presence of diabetes (Wilson P. W. et al., *Circulation.* 1998; 97:1837-1847).

Statistical analyses were performed using SPSS software (version 12.0.1; Chicago, Ill.). A P-value<0.05 was considered to indicate statistical significance.

Results

Baseline Characteristics (Table 1 and Table 2)

The baseline characteristics of cases and controls are shown in Table 1. In both men and women, the patients who developed CAD during follow-up were more likely to have a previous history of diabetes, hypertension, smoking and dyslipidemia than those who remained free of event. Higher blood pressure, LDL-C levels, CRP levels, sPLA2 activity, and lower HDL-C levels were observed in cases than in controls. sPLA2 activity was significantly associated with traditional cardiovascular risk factors, with the exception of diabetes (Table 2). Similar results were obtained for men and women (data not shown).

sPLA2 activity and risk of incident coronary artery disease (Table 3)

Among all the variables entered into the multivariable model, presence of diabetes, smoking status, systolic blood pressure, LDL-C, CRP and sPLA2 activity were independent predictors of incident CAD whereas HDL-C was associated with a reduced risk of CAD. The odds ratio of incident CAD associated with an increase of 1 nmole/min/ml of sPLA2 activity was 1.10 (1.02-1.18, P=0.01). An increase of 1 ng/ml of sPLA2 type IIA concentration was associated with an odds ratio of 1.02 (1.01-1.03, P=0.003). The odds ratio of incident CAD associated with an increase of 1 mg/l of CRP was 1.02 (1.01-1.03, P=0.02).

Table 3 presents adjusted odds ratios of incident CAD according to increasing quartiles of baseline sPLA2 activity or baseline CRP. After adjustment for all traditional risk factors, CRP and sPLA2 type IIA concentration, the odds ratios of incident CAD in the second, third and fourth quartiles of sPLA2 activity were 1.41, 1.33, and 1.56 (P=0.003), compared with the lowest quartile. Similar effects were observed in men or women (data not shown). The corresponding odds ratios associated with increasing quartiles of CRP, adjusted for traditional risk factors, sPLA2 type IIA concentration and sPLA2 activity were 0.93, 1.19, and 1.43 (P=0.001). Increasing quartiles of sPLA2 type IIA concentration were associated with a modest increase in the risk of incident CAD after adjustment for traditional risk factor, CRP and sPLA2 activity (1.02, 1.12, and 1.29, P=0.04).

sPLA2 Activity and the Framingham Risk Score

To assess whether sPLA2 activity levels had predictive value on top of the Framingham risk score, odds ratios of incident CAD per sPLA2 activity quartile were calculated by conditional logistic regression, and adjusted for components of the Framingham risk score. Increasing quartiles of sPLA2 activity remained significantly associated with the risk of future CAD 1.0 (chosen as reference), 1.4 (1.1-1.8), 1.3 (1.0-1.7), and 1.6 (1.3-2.1) (P=0.001). The corresponding odds ratios for increasing quartiles of CRP were 1.0 (chosen as reference), 1.0 (0.8-1.3), 1.3 (1.0-1.6), and 1.8 (1.4-2.3), (P<0.001).

Combined Measurement of sPLA2 Activity and CRP Levels to Assess the Risk of Incident CAD (Table 4)

sPLA2 activity and CRP levels were poorly correlated (r=0.15), suggesting each biomarker identifies different high-risk groups. The ability of the model based on sPLA2 activity to discriminate events from non events was similar to that of the model based on CRP levels. The likelihood ratio chi-square statistic was 220 for the model based on sPLA2 activity and 225 for the model based on CRP (10 df for both). The addition of sPLA2 activity to the model based on CRP significantly increased the ability of the model to predict the occurrence of incident CAD (chi-square=14.4, 1 df; P<0.001). The combined measurement of CRP and sPLA2 activity, but not sPLA2 type IIA concentration, was particularly informative. Increasing quartiles of sPLA2 activity remained associated with the risk of future CAD in people with very low CRP levels (<0.70 mg/l) (Table 4), who would have been considered at low risk of CAD. In addition, increasing quartiles of sPLA2 activity were also associated with the risk of future CAD even in people with the highest CRP levels ($\geq$3.10 mg/l) (Table 4). In contrast, increasing quartiles of sPLA2 type IIA concentration were not associated with a further increase in the risk of CAD in people with high CRP levels (Table 5). Most interestingly, people in the highest quartiles of sPLA2 activity ($\geq$4.95 nmole/min/ml) and CRP ($\geq$3.10 mg/l) (n=309) had an adjusted odds ratio of 2.89 (95% Cl, 1.78 to 4.68; P<0.001), as compared with those in the lowest quartiles of both markers (n=176) (Table 4).

Example 2

Micromethod Adaptation for Automated Fluorimetric Measurement of Serum Phospholipase A2 Activity The following method was used for sPLA2 activity determination in Example 1.

Serum samples (n=79) were obtained from healthy blood donors (34 men and 45 women; age range, 21-64 years) with written informed consent. The relationship between sPLA2 activity and the immunoreactive sPLA2 level was also determined using a human ELISA kit, in 234 patients with acute coronary syndrome, in a mean of 30 hours after the onset of ischemic symptoms. Sera were obtained from blood samples immediately centrifuged at 1000 g at 4° C. for 10 minutes and stored at −70° C. until analysed. Before analysis, the thawed samples were centrifuged at 1000 g for 60 s.

Figure 1:
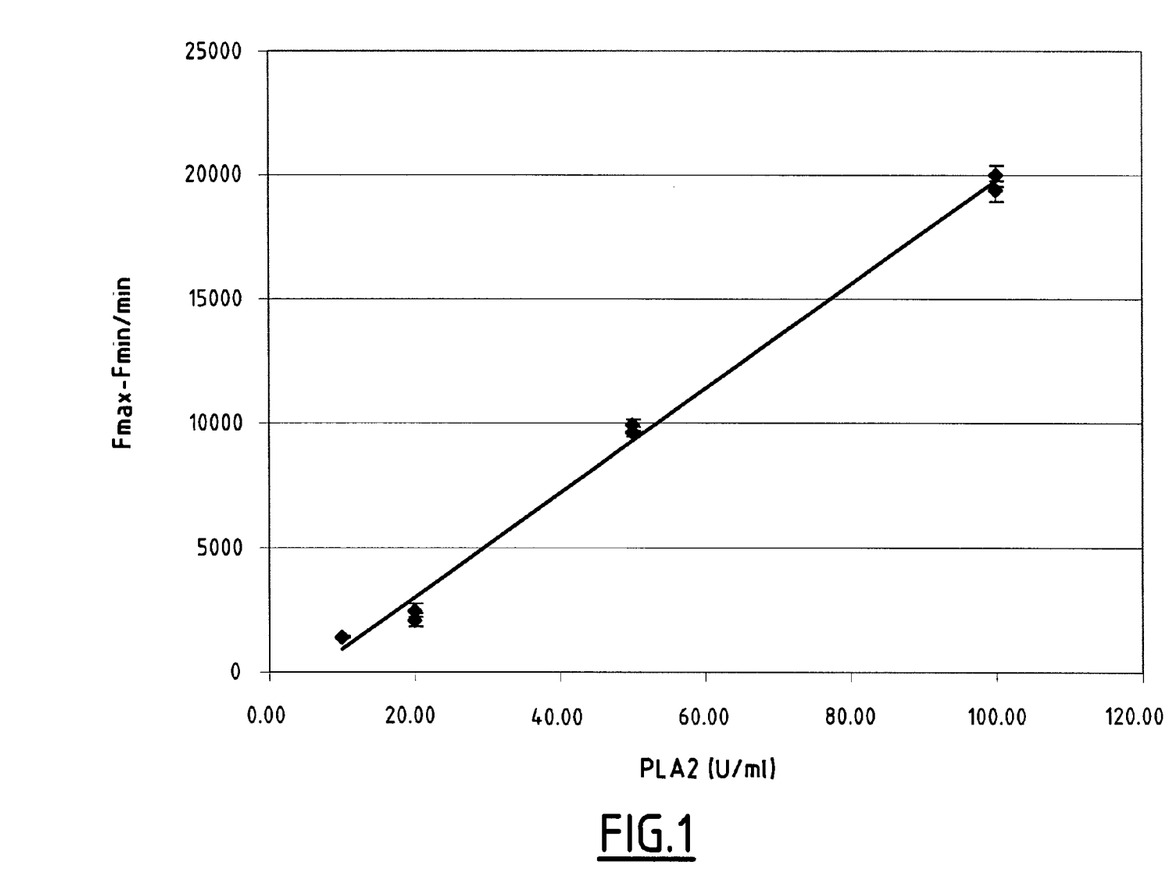
FIG. 1 represents the relationship between the difference in fluorescence (Fmax−Fmin) for one minute and the concentration of bee venom sPLA2.
Figure 2:
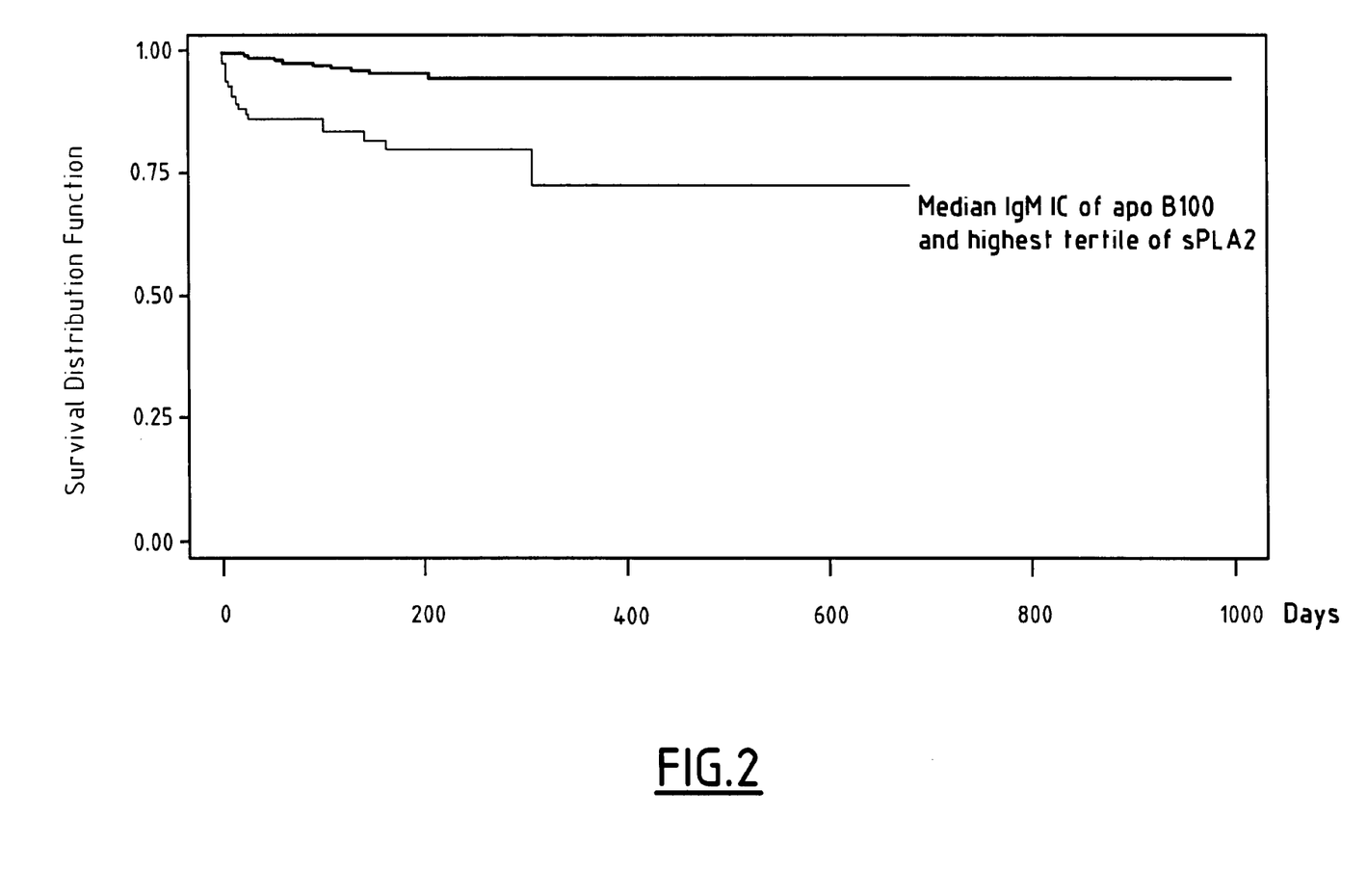
FIG. 2 represents a Kaplan-Meier analysis of the survival distribution function without myocardial infarction versus the number of days.

The PLA2 activity secreted into serum was measured in a continuous fluorimetric assay using the self-quenching properties of 1-hexadecanoyl-2-(1-pyredecanoyl)-sn-glycero-3 phosphomethanol, sodium salt (Interchim, Montluçon, France). Hydrolysis of this substrate by sPLA2 leads to an increase in fluorescence at 405 nm ($\lambda_{excitation}$ 355 nm, $\lambda_{emission}$ 405 nm). This increase in fluorescence can be used to determine the initial rate of hydrolysis of the substrate and consequently the sPLA2 activity in an unknown sample. Briefly, 1 nmol of fluorescent substrat in 200 µl of buffer (10 mM Tris-HCL, pH 8.7, 0.1% albumin, 10 mM calcium chloride) was automatically distributed in Black Maxisorp microtitration plate (96 wells). Because the self-quenching properties of the substrate, a low fluorescence is firstly recorded (Fmin) in a Fluostar Optima fluorimeter equipped with a stirring device and thermostat ruled at 30° C. The addition of 30 µl (100 U/mL) of bee venom PLA2 (Sigma Chemical Co., France) leads to a rapid hydrolysis of all substrate (100% of hydrolysis) and an increase in fluorescence to a maximal value (Fmax). The difference in fluorescence (Fmax−Fmin) is linearly related to the concentration of substrate in the buffer and was kept constant in all assays. The initial rate of substrate hydrolysis was linearly related to the amount of bee venom PLA2 added (FIG. 1). To determine the sPLA2 activity in unknown blood samples, 30 µl of sera were automatically distributed and added to the substrate mixture. The fluorescence was recorded at one minute and thus, corresponds to an activity of sPLA2 able to hydrolyse 1 nmol of substrate in one minute. A two-point procedure was used to measure the corrected fluorescence intensity of each sample and to evaluate the enzymatic activity (expressed in nmol/min/ml). All samples were tested in duplicate.

The dynamic range of this assay was limited only by the accuracy of the fluorescence measurement and the detection limit (mean+3 SD) of the sPLA2 activity fluorimetric assay was 0.15 nmol/min/ml as determined by measuring the fluorescence intensity of buffer solution. The upper limit of the assay was assessed when substrate hydrolysis was above 50%. None of abnormal samples included in this study exhibited substrate hydrolysis above 50% and needed to be diluted.

The imprecision of the sPLA2 activity fluorimetric assay was determined by measurement of samples with low (1.25 nmol/min/ml) and high (9.5 nmol/min/ml) sPLA2 activity. Within-batch CVs ranged from 2.7% (low-activity sample, n=10) to 3.2% (high-activity sample, n=10) and the between-batch CV was 5.7% (n=10). Serum sPLA2 activity was not affected by storage at −70° C. for 6 months. The mean (±SD) serum sPLA2 for healthy adults was estimated at 3.25±0.58 nmol/min/ml (ranging from 1.69 to 5.86 nmol/min/ml).

For 234 samples of patients with acute coronary syndrome, immunoreactive sPLA2 levels were measured using a human ELISA kit purchased from Cayman Chemical Company. Secretory PLA2 activities measured in these samples correlated with those determined with the immunoreactive sPLA2 measurement (p<0.0138; r=0.44). The mean of sPLA2 evaluated by these two methods were 5.57±1.88 nmol/min/ml (0.9-16.9 nmol/min/ml) and 587.7±1126.3 pg/ml (67.32-10090 pg/ml) for the activity fluorimetric measurement and the immunoreactive method; respectively.

Example 3

Human Immune Complexes of apo B100

Monoclonal antibody, MB47 (specific for human apoB100) is plated overnight at 4° C., at a concentration of 5

μg/ml, in PBS, 50 μl/well. After washing the plate 3 times with PBS, the plates are blocked using 100 μl of 1% BSA in PBS or TBS for 45 minutes at room temperature. After another wash with PBS, human plasma, diluted at 1:50 in PBS containing 1% BSA, is added to the well at 50 μl/well for 1 hour at room temperature. All plasmas are added to triplicate wells and the average used. After washing again, alkaline phosphatase-labeled goat anti-human IgG or IgM (Sigma), diluted in tris-buffered saline containing 1% BSA plus activators is added to the wells for 1 hour at room temperature, 50 μl/well. A chemiluminescent reagent, LumiPhos 530 (Lumigen, Inc) diluted 1:1 with distilled $H_2O$, is added to each well for 90 minutes, after which time the plates are read in chemiluminometer (Dynex luminometer).

To verify that equal amounts of apoB100 were captured, the above was set up but the secondary antibody, biotine-labeled goat anti-human apoB100 (BioDesign International) was added. After 1 hour at room temperature, the plate is washed and a tertiary antibody, alkaline phosphatase-labeled neutrAvidin (Pierce) is added to the wells. Then follows the chemiluminescent reagent as above.

The activators used here are a mixture of 20 mM $MgCl2$, 20 mM $ZnCl_2$, 0.4% azide and, diluted before use (1:20 in TBS/1% BSA buffer).

Example 4

Automated Fluorescent sPLA2 Assay in Human Plasma or Serum Sample

Alternatively to the method described used in Example 1 and detailed in Example 2 for measuring sPLA2 activity, the following method has been developed to take into account the variability which can be due to a non-specific increase in fluorescence intensity depending on other factors in the biological sample that may interfere with the detection of the activity of sPLA2.

The PLA2 activity secreted (sPLA2) into plasma or serum was measured in a continuous fluorimetric assay using the self-quenching properties of 1-hexadecanoyl-2-(1-pyredecanoyl)-sn-glycero-3 phosphomethanol, sodium salt (Interchim, Montluçon, France). Hydrolysis of this substrate by sPLA2 yields 1-pyrenedecanoic acid, and leads to an increase in fluorescence at 405 nm ($\lambda_{excitation}$ 355 nm, $\lambda_{emission}$ 405 nm). This increase in fluorescence can be used to determine the initial rate of hydrolysis of the substrate and consequently the sPLA2 activity in an unknown sample. The sPLA2 assay was carried out in a 96 well plate fluorimeter (i.e the Fluostar Optima in our lab from BMG Labtech). Briefly, 200 μl of working substrate solution (substrate at 5 μM final concentration in TRIS/HCL 10 mM, pH 8.7 buffer containing 10 mM CaCl2, and 0.1% final bovine serum albumin) was automatically distributed in Black Maxisorp microtitration plate (96 wells). Because the self-quenching properties of the substrate, a low fluorescence is firstly recorded for 2 minutes at 30° C. (in Plate Setting menu—orbital shaking mode: 7-cycle time: 5 seconds) to give the baseline of the reaction (Fmin). The addition of PLA2 working solution (1000 U/ml) of bee venom PLA2 (Sigma Chemical Co., France) leads to a rapid hydrolysis of all substrate (100% of hydrolysis) and an increase in fluorescence to a maximal value (Fmax). The gain of the fluorimeter may be automatically adjusted on the 100% of hydrolysis. The difference in fluorescence (Fmax−Fmin) is linearly related to the concentration of substrate in the buffer and was kept constant in all assays. To determine the sPLA2 activity in unknown blood samples, the reaction is initiated by 30-50 μl of plasma or serum sample automatically distributed and added to the substrate mixture. One line of 12 wells was assayed at a time and all samples were tested in duplicate. The fluorescence was recorded for 3 to 5 minutes depending on the slope and the slope per minute was determined. To convert the slope per minute (F) into activity (A) of sPLA2 expressed in nmol/min/ml, the calculus is given by the following formula:

$$A(\text{nmole/ml/min}) = \frac{F(\text{slope per minute}) \times 1 \cdot \text{nmole}}{(F\text{max} - F\text{min}) \times V(\text{ml})}$$

1 nmole is contained in the working substrate solution at a concentration of 5 μM
V is the sample volume expressed in ml (0.30 to 0.50 ml)
(Fmax−Fmin) the maximal fluorescence signal at the end of the reaction in the presence of PLA2 from bee venom.
F is the calculated slope per minute The mean (±SD) plasma sPLA2 activity measured in a healthy adult population (n=2282) was estimated at 1.63±0.62 nmol/min/ml. Quartiles were based on the distribution in the population and the sPLA2 activity quartiles distribution found is: quartile 1 corresponds to the part of the given population with the lowest sPLA2 activity (0.01 to 1.22 nmole/min/ml), quartile 2 corresponds to values ranging from 1.22 to 1.54 nmole/min/ml, quartile 3 corresponds to values ranging from 1.54 to 1.93 nmole/min/ml and quartile 4 corresponds to the part of the population with the higher sPLA2 activity (>1.93 nmole/min/ml).

TABLE 1

Baseline characteristics of study participants

|  | Controls | Cases | P |
|---|---|---|---|
| Men, n | 1138 | 633 |  |
| Age, years | 65 ± 8 | 65 ± 8 | Matched |
| Body mass index, kg/m2 | 26.2 ± 3.0 | 27.2 ± 3.5 | <0.001 |
| Diabetes, % (n) | 2.0 (23) | 6.8 (43) | <0.001 |
| Smoking |  |  |  |
| current, % (n) | 8.4 (96) | 16.1 (102) | <0.001 |
| previous, % (n) | 59.5 (677) | 58.6 (371) | <0.001 |
| never, % (n) | 32.1 (365) | 25.3 (160) | <0.001 |
| Systolic blood pressure, mmHg | 139 ± 18 | 144 ± 19 | <0.001 |
| Diastolic blood pressure, mmHg | 85 ± 11 | 86 ± 12 | <0.001 |
| Total cholesterol, mmol/l | 6.0 ± 1.1 | 6.3 ± 1.1 | <0.001 |
| LDL-c, mmol/l | 4.0 ± 1.0 | 4.2 ± 1.0 | <0.001 |
| HDL-c, mmol/l | 1.2 ± 0.3 | 1.2 ± 0.3 | <0.001 |

TABLE 1-continued

Baseline characteristics of study participants

|  | Controls | Cases | P |
|---|---|---|---|
| Triglycerides, mmol/l* | 1.7 (1.2-2.3) | 1.9 (1.4-2.7) | <0.001 |
| CRP, mg/l* | 1.4 (0.7-2.9) | 2.1 (1.0-4.5) | <0.001 |
| sPLA2, ng/ml* | 7.3 (5.3-10.9) | 8.3 (5.8-12.7) | <0.001 |
| sPLA2 activity, nmole/min/ml* | 4.2 (3.7-4.9) | 4.5 (4.0-5.2) | <0.001 |
| Women, n | 668 | 358 |  |
| Age, years | 66 ± 7 | 67 ± 7 | Matched |
| Body mass index, kg/m2 | 26.1 ± 3.8 | 27.3 ± 4.6 | <0.001 |
| Diabetes, % (n) | 0.9 (6) | 5.3 (19) | <0.001 |
| Smoking |  |  |  |
| current, % (n) | 8.1 (54) | 15.4 (55) | <0.001 |
| previous, % (n) | 36.2 (242) | 38.8 (139) | <0.001 |
| never, % (n) | 55.7 (372) | 45.8 (164) | <0.001 |
| Systolic blood pressure, mmHg | 138 ± 19 | 142 ± 19 | 0.002 |
| Diastolic blood pressure, mmHg | 82 ± 11 | 84 ± 12 | 0.001 |
| Total cholesterol, mmol/l | 6.6 ± 1.1 | 6.8 ± 1.3 | <0.001 |
| LDL-c, mmol/l | 4.3 ± 1.1 | 4.5 ± 1.1 | <0.001 |
| HDL-c, mmol/l | 1.6 ± 0.4 | 1.4 ± 0.4 | <0.001 |
| Triglycerides, mmol/l* | 1.5 (1.1-2.1) | 1.8 (1.3-2.4) | <0.001 |
| CRP, mg/l* | 1.6 (0.7-3.4) | 2.6 (1.1-6.0) | <0.001 |
| sPLA2, ng/ml* | 10.4 (7.2-16.3) | 12.4 (8.0-18.4) | <0.001 |
| sPLA2 activity, nmole/min/ml* | 4.3 (3.8-5.1) | 4.8 (4.0-5.6) | <0.001 |
| Men and Women, n | 1806 | 991 |  |
| Age, years | 65 ± 8 | 65 ± 8 | Matched |
| Body mass index, kg/m2 | 26.2 ± 3.3 | 27.3 ± 3.9 | <0.001 |
| Diabetes, % (n) | 1.6 (29) | 6.3 (62) | <0.001 |
| Smoking |  |  |  |
| current, % (n) | 8.3 (150) | 15.8 (157) | <0.001 |
| previous, % (n) | 50.9 (919) | 51.5 (510) | <0.001 |
| never, % (n) | 40.8 (737) | 32.7 (324) | <0.001 |
| Systolic blood pressure, mmHg | 139 ± 18 | 144 ± 19 | <0.001 |
| Diastolic blood pressure, mmHg | 84 ± 11 | 86 ± 12 | <0.001 |
| Total cholesterol, mmol/l | 6.2 ± 1.1 | 6.5 ± 1.2 | <0.001 |
| LDL-c, mmol/l | 4.1 ± 1.0 | 4.3 ± 1.1 | <0.001 |
| HDL-c, mmol/l | 1.4 ± 0.4 | 1.3 ± 0.4 | <0.001 |
| Triglycerides, mmol/l* | 1.5 (1.1-3.4) | 1.8 (1.3-2.6) | <0.001 |
| CRP, mg/l* | 1.6 (0.7-3.4) | 2.2 (1.0-5.0) | <0.001 |
| sPLA2, ng/ml* | 10.4 (7.2-16.3) | 9.5 (6.4-15.0) | <0.001 |
| sPLA2 activity, nmole/min/ml* | 4.3 (3.8-5.1) | 4.6 (4.0-5.3) | <0.001 |

Values represent mean ± SD.
*Values represent medians and interquartile ranges.

TABLE 2

Base-line characteristics of cases and controls according to quartiles of sPLA2 activity

|  | sPLA2 activity quartiles | | | | P |
|---|---|---|---|---|---|
|  | 1 | 2 | 3 | 4 |  |
| sPLA2 activity, nmole/min/ml | <3.74 | [3.74-4.29[ | [4.29-4.95[ | ≥4.95 |  |
| Age, years | 64 ± 8 | 65 ± 8 | 65 ± 8 | 66 ± 8 | <0.001 |
| Body mass index, kg/m2 | 25.9 ± 3.4 | 26.3 ± 3.5 | 26.7 ± 3.6 | 27.2 ± 3.7 | <0.001 |
| Diabetes, % (n) | 2.5 (15) | 3.7 (25) | 4.0 (28) | 2.9 (23) | 0.4 |
| Smoking |  |  |  |  |  |
| current, % (n) | 7.4 (45) | 11.3 (77) | 11.8 (83) | 12.8 (102) |  |
| previous, % (n) | 53.4 (326) | 45.8 (313) | 50.3 (354) | 54.5 (436) | <0.001 |
| never, % (n) | 39.2 (239) | 42.9 (293) | 37.9 (267) | 32.8 (262) |  |
| Systolic blood pressure, mmHg | 138 ± 18 | 139 ± 18 | 141 ± 19 | 143 ± 18 | <0.001 |
| Diastolic blood pressure, mmHg | 83 ± 11 | 83 ± 11 | 85 ± 12 | 86 ± 12 | <0.001 |
| Total cholesterol, mmol/l | 5.9 ± 1.0 | 6.1 ± 1.1 | 6.3 ± 1.1 | 6.8 ± 1.2 | <0.001 |
| LDL-c, mmol/l | 3.9 ± 0.9 | 4.0 ± 1.0 | 4.1 ± 1.0 | 4.4 ± 1.1 | <0.001 |
| HDL-c, mmol/l | 1.4 ± 0.4 | 1.4 ± 0.4 | 1.3 ± 0.4 | 1.3 ± 0.4 | <0.001 |
| Trigs, mmol/l | 1.4 ± 0.6 | 1.6 ± 0.6 | 1.9 ± 0.8 | 2.4 ± 1.0 | <0.001 |
| CRP, mg/l | 3.1 ± 5.3 | 3.2 ± 4.8 | 3.7 ± 5.9 | 4.5 ± 7.1 | <0.001 |
| sPLA2 type IIA, ng/ml | 9.6 ± 8.7 | 10.7 ± 8.1 | 11.3 ± 9.1 | 13.3 ± 10.2 | <0.001 |

Values represent mean ± SD.

TABLE 3

Adjusted odds ratios of incident coronary artery disease during follow-up according to quartiles of sPLA2 activity or CRP, measured at baseline

| | sPLA2 activity quartiles (nmole/min/ml) | | | | |
|---|---|---|---|---|---|
| | 1 | 2 | 3 | 4 | P |
| | <3.74 | [3.74-4.29[ | [4.29-4.95[ | ≧4.95 | |
| Cases/controls | 160/450 | 230/453 | 252/452 | 349/451 | |
| Model 1 (95% CI) | 1.00 | 1.41 (1.10-1.83) | 1.38 (1.07-1.78) | 1.70 (1.32-2.19) | <0.001 |
| Model 2 (95% CI) | 1.00 | 1.43 (1.10-1.84) | 1.36 (1.05-1.76) | 1.65 (1.27-2.12) | 0.001 |
| Model 3 (95% CI) | 1.00 | 1.41 (1.09-1.82) | 1.33 (1.03-1.72) | 1.56 (1.21-2.02) | 0.003 |

Model 1: Matched for sex, age, enrolment time, and adjusted for diabetes, smoking, BMI, systolic BP, LDL-C, HDL-C
Model 2: Model 1 with further adjustment for Log(CRP)
Model 3: Model 2 with further adjustment for Log(sPLA2 type IIA concentration)

| | CRP quartiles (mg/l) | | | | |
|---|---|---|---|---|---|
| | 1 | 2 | 3 | 4 | P |
| | <0.70 | [0.70-1.45[ | [1.45-3.10[ | ≧3.10 | |
| Cases/controls | 160/434 | 192/465 | 256/468 | 383/439 | |
| Model 1 (95% CI) | 1.00 | 0.94 (0.72-1.22) | 1.22 (0.94-1.58) | 1.61 (1.25-2.08) | <0.001 |
| Model 2 (95% CI) | 1.00 | 0.92 (0.71-1.21) | 1.20 (0.93-1.56) | 1.55 (1.20-1.99) | <0.001 |
| Model 3 (95% CI) | 1.00 | 0.93 (0.71-1.22) | 1.19 (0.91-1.54) | 1.43 (1.11-1.86) | 0.001 |

Model 2: Model 1 with further adjustment for Log(sPLA2 activity)
Model 3: Model 2 with further adjustment for Log(sPLA2 type IIA concentration)

TABLE 4

Adjusted odds ratios of incident coronary artery disease during follow-up according to combined quartiles of sPLA2 activity or CRP, measured at baseline

| CRP quartiles (mg/l) | sPLA2 activity quartiles (nmole/min/ml) | | | |
|---|---|---|---|---|
| | 1 <3.74 | 2 [3.74-4.29[ | 3 [4.29-4.95[ | 4 ≧4.95 |
| 1 (<0.70) | 1.00 | 1.43 (0.82-2.49) | 1.62 (0.93-2.64) | 1.94 (1.10-3.41) |
| 2 ([0.70-1.45[) | 1.06 (0.60-1.89) | 1.37 (0.79-2.36) | 1.39 (0.82-2.37) | 1.63 (0.96-2.78) |
| 3 [1.45-3.10[ | 1.50 (0.86-2.61) | 2.21 (1.30-3.75) | 1.57 (0.93-2.64) | 1.94 (1.16-3.25) |
| 4 (≧3.10) | 1.55 (0.89-2.69) | 2.25 (1.34-3.78) | 2.51 (1.49-4.23) | 2.89 (1.78-4.68) |

Odds ratios calculated by conditional logistic regression taking into account matching for sex, age, enrolment time, and adjusting for diabetes, smoking, body mass index, systolic blood pressure, LDL-c, and HDL-c

TABLE 5

Median and quartiles values of IgM IC of apo B100 and IgM of MDA-LDL determined by the method of example 3.

| Variable | Median (RLU) | Lower Quartile (RLU) | Upper Quartile (RLU) | Quartile Range (RLU) |
|---|---|---|---|---|
| IgMIC of apoB100 | 1909.68 | 1373.17 | 2922.80 | 1549.63 |
| MDA-LDL IgM | 9229.17 | 6235.70 | 13967.3 | 7731.65 |

TABLE 6

Odds ratio of the lower median of IgM IC of apo B100 and the highest tertile of sPLA

| Variable | Pr > ChiSq | Hazard Ratio | 95% Hazard Ratio Confidence Limits | |
|---|---|---|---|---|
| Lower Median of IgMIC + tertile 3 PLA2 | <.0001 | 4.995 | 2.457 | 10.155 |

(N = 85)

The invention claimed is:

1. A method for determining an increased risk of mortality or risk of a cardiac and/or vascular event in a patient, wherein said cardiac and/or vascular event is selected from the group consisting of myocardial infarction, vascular cerebral accident, hospitalization due to cardiac and/or vascular disease, and revascularization procedure, the method comprising:

determining a value of secretory phospholipase A2 (sPLA2) activity of said patient as a first risk marker, wherein the sPLA2 activity is measured from a blood sample of said patient, and locating this value in an interval of a set of predetermined intervals of sPLA2 activity range obtained from a given population, wherein said predetermined intervals are medians, tertiles, quartiles or quintiles of sPLA2 activity range of said given population, determining a value of C-reactive protein (CRP) level of said patient as a second risk marker, wherein the CRP level is measured from a blood sample of said patient, and locating this value in an interval of a set of predetermined intervals of CRP level obtained from said given population, wherein said predetermined intervals are medians, tertiles, quartiles or quintiles of CRP level range of said given population and, assessing a combined interval obtained by combining the two above mentioned intervals of said patient, said combined interval being indicative of an increased risk of mortality or risk of a cardiac and/or vascular event in the patient.

2. The method according to claim 1, wherein the sPLA2 activity is measured from a plasma sample of the patient and is higher than about 1.22 nmol/ml/min, or the sPLA2 activity is measured from a serum sample of the patient and is higher than about 3.74 nmol/ml/min.

3. The method according to claim 1, wherein the CRP level is measured from a serum sample of the patient and is higher than 0.70 mg/l.

4. The method according to claim 1, wherein the patient is diagnosed as being substantially healthy with respect to atherosclerosis, cardiac and/or vascular related diseases.

5. The method according to claim 1, wherein the patient is diagnosed as presenting at least one of the following coronary disorders:

asymptomatic artery diseases with silent ischemia or without ischemia, chronic ischemic disorders without myocardial necrosis, stable angina pectoris or effort angina pectoris, acute ischemic disorders without myocardial necrosis or unstable angina pectoris, ischemic disorders with myocardial necrosis, ST segment elevation myocardial infarction or non-ST segment elevation myocardial infarction.

6. The method according to claim 1, wherein no onset of ischemic symptoms has been diagnosed in the patient.

7. The method according to claim 1, wherein an onset of ischemic symptoms has been diagnosed in the patient.

8. A method for the prognosis and the diagnosis of cardiovascular disorders, comprising using a combined value measured from the blood samples of markers sPLA2 activity and CRP level for the prognosis and the diagnosis of cardiovascular disorders.

9. A method for determining an increased risk of developing a cardiovascular disease in a patient, comprising:
  measuring in a blood sample two markers: secretory phospholipase A2 (sPLA2) activity, and C-reactive protein (CRP) level;
  combining said measurements into a combined value and assessing the risk of the patient to develop a cardiovascular disease based on the combined measurements.

* * * * *